United States Patent [19]

Kirsch et al.

[11] 4,124,768

[45] Nov. 7, 1978

[54] PROCESS FOR PREPARING PURE SUBSTITUTED 2,5-DIARYLAMINO-TEREPHTHALATES AND THE CORRESPONDING FREE ACIDS

[75] Inventors: Aloys Kirsch; Otto Fuchs, both of Frankfurt am Main; Ernst Spietschka, Idstein, Taunus, all of Fed. Rep. of Germany

[73] Assignee: Hoechst Aktiengesellschaft, Frankfurt am Main

[21] Appl. No.: 725,501

[22] Filed: Sep. 22, 1976

[30] Foreign Application Priority Data

Sep. 24, 1975 [DE] Fed. Rep. of Germany ....... 2542494

[51] Int. Cl.$^2$ ........................................... C07D 101/68
[52] U.S. Cl. ....................................... 560/19; 560/45; 560/47; 560/48; 106/288 Q; 546/49
[58] Field of Search ............... 260/471 R; 560/19, 47, 560/48, 45

[56] References Cited

U.S. PATENT DOCUMENTS 3,388,149  1/1964   Chi Kang Dien .................. 260/471

FOREIGN PATENT DOCUMENTS 891,640  3/1962   United Kingdom ..................... 260/471
911,476 11/1962   United Kingdom ..................... 260/471

*Primary Examiner*—Donald G. Daus
*Assistant Examiner*—Lisa Jones
*Attorney, Agent, or Firm*—Curtis, Morris & Safford

[57] ABSTRACT

2,5-Diarylamino terephthalates are obtained in good yields and excellent purity when the aromatic nitro compound used for oxidizing the corresponding dihydro-2,5-diarylamino terephthalate contains the aromatic radical of said diarylamino groups, i.e. when the amine formed during the oxidation is that from which said diarylamino groups device. The products yield very pure quinacridone pigments and allow the synthesis of only one isomer of substituted quinacridones.

17 Claims, No Drawings

PROCESS FOR PREPARING PURE SUBSTITUTED 2,5-DIARYLAMINO-TEREPHTHALATES AND THE CORRESPONDING FREE ACIDS 2,5-Diarylaminoterephthalic acids are starting materials for the preparation of quinacridones. The purity of these starting materials is important for the reproducibility of the synthesis and for the subsequent formation of the pigment.

It is already known how to prepare 2,5-diarylaminoterephthalic acid esters by oxidation of the corresponding dihydro compound with nitrobenzene (British Pat. No. 911,476). The nitrobenzene may also serve as solvent, if desired, already in the preparation of the 2,5-diarylaminodihydroterephthalates from the aromatic amine and a succinylo-succinic acid ester.

It has now been found that in this synthesis unhomogeneous products are formed if the arylamine is different from aniline. If the amine is p-toluidine there are obtained besides the 2,5-di-p-toluidino compound considerable amounts of 2-anilino-5-toluidino compound and occasionally even detectable amounts of bis-anilino compound. These compounds are obtained due to the fact that aniline formed by reduction of the nitrobenzene influences the process of the reaction. On the one hand a transamination in the 2,5-diarylaminodihydroterephthalates may take place, especially if the amino radical displaced is less basic than the aniline. On the other hand the aniline can react with succinylo-succinic acid ester not yet reacted or condensed only on one side, if already during the condensation phase oxidation (and thus a formation of aniline) takes place. It has now been found that uniform 2,5-diarylaminoterephthalates are obtained if for the oxidation of the dihydro compound the nitro compound corresponds to the arylamine used.

Thus, the invention relates to a process for the preparation of a compound of the formula (I)

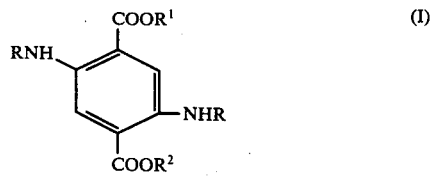

wherein $R^1$ and $R^2$ are identical or different and represent alkyl groups having 1 to 5 carbon atoms and R is a substituted phenyl radical or an optionally substituted naphthyl radical, each of it having at least one free ortho position, from a compound of the formula (II)

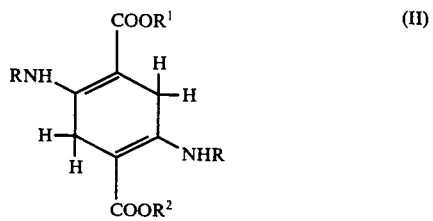

wherein R, $R^1$, and $R^2$ have the meanings mentioned, by oxidation with aromatic nitro compounds in the presence of acids and if desired, subsequent saponification to the free acid, in which process the nitro compound has the formula (III)

$$R - NO_2 \quad (III)$$

wherein R has the above meaning.

From Example 5 of German Offenlegungsschrift No. 1,493,419 it is already known to oxidize diethyl-2,5-bis-(p-toluidino)-dihydroterephthalate with p-nitrotoluene, however this reaction is effected in aqueous ethanolic sodium hydroxide solution with simultaneous saponification of the ester groups. But under these reaction conditions there are considerable side-reactions, probably already on the level of the dihydro compound which has to be considered as derivative of a β-keto ester. This leads to a reduction in yield and quality of product.

Preferred variants of the process of the invention are described in the following:

As nitro compound of the formula (III) there is preferably chosen a compound, in which R is a group of the formula (IV)

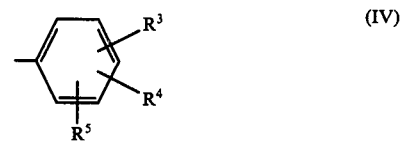

wherein $R^3$, $R^4$ and $R^5$ represent hydrogen, halogen, alkyl groups having 1 to 5 carbon atoms, alkoxy groups having 1 to 5 carbon atoms, phenyl, phenoxy or two of the radicals $R^3$, $R^4$ and $R^5$ together represent a fused benzene nucleus, with the proviso that at least one of the radicals $R^3$, $R^4$ and $R^5$ is different from hydrogen and at least one ortho-position to the nitrogen atoms is unsubstituted.

The process of the invention provides with an excellent yield uniform pure 2,5-arylaminoterephthalic acids. These properties of the acids are very important for their capacity of being used as starting material for the preparation of high quality quinacridone pigments in a reproducible way.

Uniform arylaminoterephthalic acids which are not contaminated by quinacridone-forming by-products are also a condition for the preparation of pure uniformly substituted quinacridones. To obtain these products free from isomers the starting compounds are arylaminoterephthalic acids of the formula (I), in which R is 1-naphthyl or R is 2-naphthyl or phenyl, in which last mentioned two groups an ortho-position is substituted by a substituent. If R stands for phenyl in which both ortho-positions are unsubstituted there are obtained quinacridones free from isomers if there is one single substituent in para-position or if there are identical substituents in 3 and 5 positions or if, in the case of a 3,4,5-trisubstitution the substituents in 3 and 5 position are identical.

A suitable nitro compounds there are considered: o-, m- and p-chloro-, -bromo-, -fluoro-, -methyl- and -methoxy-nitrobenzene, 2-chloro-4-methyl-nitrobenzene, 3-chloro-4-methyl-nitrobenzene, 2,4-dichloronitrobenzene, 2,3-dichloro-nitrobenzene or 2,3,4-trichloro-nitrobenzene as well as 1- and 2-nitronaphthalene. There are preferred m-chloronitrobenzene, p-nitrotoluene and o- and p-chloronitrobenzene.

The oxidation of the compound (III) is effected in the presence of catalytic amounts of acid. There may be used inorganic acids, such as mineral acids, or organic acids such as glacial acetic acid or trifluoroacetic acid. As oxidating accelerator there may be additionally added a secondary or tertiary amine, for example piperidine.

It is possible to carry out the oxidation in the presence of inert diluents or solvents. But the nitro compound is preferably used in excess.

Depending on the temperature of the process and the physical properties of the reaction products the amount of the nitro compound is expediently chosen in such a way that a phase capable of being stirred is obtained in the condensation step. Since the oxidation product is much better soluble than the dihydro compound the solubility increases with progressive oxidation until the reaction product is completely dissolved. As soon as a clear reaction solution is obtained it may be taken for granted that oxidation is finished.

In a specially preferred variant of the invention the 2,5-diarylamino-3,6-dihydro-terephthalic acid ester of the formula (II) is synthetized in situ from the succinylo-succinic acid ester of the formula (V)

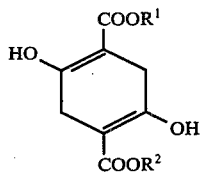

(V)

and the at least double molar amount of the amine of the formula (VI)

R — NH$_2$

The nitro compound of the formula (III) is also used as solvent and diluent. The condensation is preferably carried out at temperatures of from 75° to 120° C. and the dihydroester thus obtained of the formula (II) is oxidized without any intermediate isolation with addition of the above-mentioned catalytic agents at temperatures of from about 110° to 150° C. to obtain the terephthalate of the formula (I) ($R^1$, $R^2$ = H). This oxidation product may be precipitated and isolated from the reaction mixture by addition of a solvent which does not dissolve well the compound (I), for example a lower alkanol, such as methanol or ethanol, and subsequently saponified.

The free acid is prepared from the terephthalic acid diester preferably without isolation of the oxidation product. The hot oxidation mixture is added to a concentrated aqueous alkali metal hydroxide solution and the ester saponification is carried out with intense agitation at temperatures of from 90° to 110° C., preferably 100° to 105° C.

The hydrolysis of esters of alkanols having low boiling points is expediently carried out in a closed vessel, so that the alcohol formed may serve as solubilizer between the organic phase containing the ester, the nitro compound and the arylamine, and the aqueous alkaline phase and thus, accelerate saponification. When the saponification is finished the alcohol is separated by distillation, and the reaction mixture is introduced, while stirring well, into about 8 to 20 times, preferably 10 to 15 times, the amount by weight, calculated on the succinylo-succinic acid ester, of water heated to 50° to 60° C., whereby the alkali salt of the 2,5-diarylaminoterephthalic acid is extracted from the organic phase. To separate phases the heavier organic phase is allowed to deposit or the mixture homogenized by stirring intensely may be separated by a centrifuge. From the aqueous phase any volatile organic contaminations present may be eliminated by steam distillation and unsoluble contaminations by filtration, if desired with the aid of a clarifying agent. From the aqueous-alkaline solution the acid is precipitated with an inorganic acid, especially a mineral acid, or a strong organic acid such as acetic acid in the pH range of 4.5 to 5.5, isolated, then washed and dried. Thus, the free acid is obtained in a very well crystalline pure form with yields of from 90 to 96% of the theory. A contamination by the above-mentioned derivatives of the aniline is not detectable.

The remaining organic phase may be regenerated by simple distillation and used again without any further purification since it consists only of the starting products, i.e. the arylamine and the corresponding nitro compound.

The process of the invention is not only characterized by the excellent purity of the product of the invention but also by the fact that no reaction step requires any additional solvent. The use of the less expensive nitro compound as diluent permits the use of stoichiometric amounts or only relatively small excesses of the expensive arylamine. Depending on the reactivity of the arylamine it may be advantageous to use about 2.5 to 4 mols of arylamine per mol of succinylo-succinic acid ester to obtain good yields in short reaction times. As compared with the known processes requiring additionally inert solvents the process of the invention is characterized by a much better space yield. Since furthermore the reaction times of about 1.5 to 4 hours for the condensation and about 2 to 4 hours for the oxidation are very favorable, the space-time yield of the process of the invention is also excellent. Thus, the expenditure in equipment and the costs can be considerably reduced.

The following Examples illustrate the invention. Parts and percentages are by weight unless stated otherwise. The ratio of parts by weight to parts by volume is that of the kilogram to the liter.

EXAMPLE 1

100 parts of succinylo-succinic acid dimethyl ester, 180 parts of 3-chloroaniline and 160 parts of 3-chloronitrobenzene are heated under nitrogen while stirring to 70° C. and mixed with 4 parts of a 33% hydrochloric acid. Stirring of the mixture is continued for 10 minutes at this temperature. Then the temperature is increased to 100° C. and a thick deposit is precipitated. The reaction mixture is stirred for 4 hours at 100° to 105° C. while distilling off water under slightly reduced pressure of 350 to 400 mm mercury. When condensation is finished one part of piperidine is added and stirring is continued for another 4 hours at 130° to 135° C. During this operation the dihydroester is dissolved with oxidation to obtain the terephthalic acid ester.

The solution thus obtained is transferred into an autoclave which contains 220 parts of a 20% sodium hydroxide solution and the mixture is stirred thoroughly for 90 minutes at 100° to 105° C.

For another 90 minutes a methanol — water mixture is distilled off until the internal temperature has reached again 105° C. Then the saponification mixture is added to 1200 parts of water and thoroughly stirred for 30 minutes at 70° C. After the deposit of the organic phase 235 parts of a mixture of chloronitrobenzene and chloroaniline, in which contaminations are dissolved, are separated. The aqueous alkaline phase is subjected to steam distillation until no more volatile constituents pass over, mixed with 3 parts of kieselguhr and clarified at 90° C. By addition of 90 parts of glacial acetic acid (pH value 4.8) the 2,5-bis(m-chlorophenylamino)-terephthalic acid is precipitated, then filtered hot, washed and dried under reduced pressure. The yield is 95.2% of the theory, calculated on the succinylo-succinic acid dimethyl ester used. Content of chlorine: 17.0% (calculated 17.0%).

If instead of 3-chloro-nitrobenzene nitrobenzene is used a product having a content of chlorine of 15.2% is obtained. In the thin-layer chromatogram the by-product 2-anilino-5-(m-chloroanilino)-terephthalic acid is detectable.

EXAMPLE 2

25 Parts of 2,5-bis-(2,3-dichloroaniline)-dihydroterephthalic acid diethyl ester (content of chlorine: 25.5%, calculated: 26.1%) are oxidized by stirring for 5 hours at 140° C. in 125 parts of 2,3-dichloronitrobenzene with addition of 5 parts of glacial acetic acid and one part of piperidine. The terephthalic acid ester is precipitated with methanol from the reaction solution, suction-filtered, washed with methanol and dried. Thus, the 2,5-bis-(2,3-dichlorophenylamino)-terephthalic acid diethyl ester is obtained in the form of orange red crystals having a melting point of 265° to 266° C. in a 95% yield, with a content of chlorine of 25.2% (calculated: 26.2%). If instead of the 2,3-dichloronitrobenzene nitrobenzene is used, a product having a content of chlorine of 22.7% is obtained.

EXAMPLE 3

20 parts of 2,5-bis-(m-chloroanilino)-dihydroterephthalic acid diethyl ester are oxidized by heating for three hours to 125° to 130° C. with 40 parts of m-chloronitrobenzene, with addition of 2 parts of glacial acetic acid and 0.6 part of piperidine. The 2,5-bis-(m-chloroanilino)-terephthalic acid diethyl ester is obtained having a content of chlorine of 14.7% (calculated: 15.0%).

If instead of m-chloronitrobenzene nitrobenzene is used for the oxidation of a product having a content of chlorine of 13.3% is obtained.

EXAMPLE 4

A mixture of 100 parts of succinylo-succinic acid dimethyl ester, 180 parts of p-toluidine and 300 parts of p-nitrotoluene is heated under nitrogen to 65° to 70° C., mixed with 4 parts of a 33% hydrochloric acid and stirred for 15 minutes. With a slightly reduced pressure the temperature is increased to 90° to 95° C. within one hour, while a thick but well stirrable deposit is precipitated and the water formed is distilled off. After stirring for three hours at 105° to 110° C. the condensation is finished. After addition of 4 parts of piperidine and 5 parts of glacial acetic acid the temperature is increased to 135° to 140° C. After stirring for 4 hours at this temperature the reaction mixture is completely dissolved and the oxidation is finished. The solution is mixed under nitrogen with 235 parts of a 20% sodium hydroxide solution and stirred thoroughly in a closed vessel at 100° to 105° C. After cooling to 85° to 90° C. a methanol-water mixture is distilled off for another 90 minutes until the temperature has reached again 105° C.

The saponification mixture is added to 600 parts of water and stirred thoroughly for 15 minutes. The organic phase which essentially consists of p-nitrotoluene and p-toluidine is allowed to deposit and then separated. The volatile constituents are eliminated from the aqueous alkaline sodium salt solution by steam distillation, the solution is clarified at 90° C. after addition of 5 parts of a clarifying agent and adjusted at 80° to 90° C. within one hour with 115 parts of a 85% phosphoric acid to pH 5. The 2,5-di-p-toluidino-terephthalic acid is precipitated in a well crystalline form. It is filtered at 80° C., washed free from phosphate ions and dried. The yield is 95% of the theory, calculated on succinylo-succinic acid dimethyl ester.

If instead of succinylo-succinic acid dimethyl ester the corresponding amount of diethyl ester is used the same result is obtained. Due to the better solubility of the ethyl ester the amount of p-nitrotoluene may be reduced to 200 parts.

If instead of p-nitrotoluene nitrobenzene is used 2-anilino-5-(p-toluidino)-terephthalic acid can be detected as by-product in the reaction product by thin-layer chromatography.

EXAMPLE 5

100 parts of succinylo-succinic acid diethyl ester, 125 parts of 5-chloro-2-aminotoluene and 400 parts of 5-chloro-2-nitrotoluene are heated under nitrogen to 115° C. After addition of one part of 33% hydrochloric acid the mixture is heated for one hour to 120° C.; after cooling to 110° C. 50 parts of glacial acetic acid and two parts of piperidine are added and the mixture is refluxed for two hours. While distilling off water and acetic acid the mixture is stirred for 90 minutes at 130° to 135° C. and the hot reaction mixture is added to 1500 parts of ethanol. After cooling the ester is suction-filtered, washed with ethanol and dried. The yield is 91% of theory, the content of chlorine is 14.2% (calculated: 14.1%).

If instead of 5-chloro-2-nitrotoluene nitrobenzene is used a product having a content of chlorine of 12.7% is obtained.

EXAMPLE 6

50 parts of succinylo-succinic acid dimethyl ester, 70 parts of 2-aminoanisole and 125 parts of 2-nitroanisole are mixed at 70° C. with two parts of 33% hydrochloric acid and stirred for two hours at 115°–120° C. under nitrogen and slightly reduced pressure (350 to 400 torr). After addition of two parts of glacial acetic acid and one part of piperidine the mixture is oxidized for two hours at 130° to 135° C. After working up as in Examples 1 and 3 the 2,5-bis(2-anisidino)-terephthalic acid is obtained with a yield of 91% of the theory.

If instead of 2-nitroanisole nitrobenzene is used the 2-anilino-5-(o-anisidino)-terephthalic acid can be identified as by-product in the thin-layer chromatogram of the reaction product.

EXAMPLE 7

If in Example 6 the 2-aminoanisole is replaced by o-chloro-aniline and the 2-nitroanisole by o-chloronitrobenzene, there are obtained under the same conditions 2,5-bis-(o-chloroanilino)-terephthalic acid having a content of chlorine of 16.2% (calculated: 17.0%).

If instead of o-chloronitrobenzene nitrobenzene is used the reaction product contains 15.1% of chlorine.

EXAMPLE 8

60.0 parts of succinylo-succinic acid ethyl ester, 90.0 parts of m-chloroaniline, 10.0 parts of glacial acetic acid and 100.0 parts of m-chloronitrobenzene are stirred under nitrogen for one hour at 100° to 105° C. and subsequently after addition of one part of piperidine for another hour at 120° to 125° C. With a good yield the 2,5-bis-(m-chloroanilino)-terephthalic acid diethyl ester is obtained having a melting point of 145° to 146° C. and a content of chlorine of 14.9% of the theory (calculated: 15.0%).

When using nitrobenzene under the same conditions the reaction product contains 13.3% of chlorine.

EXAMPLE 9

50.0 parts of succinylo-succinic acid dimethyl ester, 100.0 parts of 1-aminonaphthalene and 150.0 parts of 1-nitronaphthalene are heated under nitrogen to 65° to 70° C., mixed while stirring with 4 parts of 33% hydrochloric acid and stirring is continued for 15 minutes. The mixture is heated within one hour to 115° C., and the water formed is eliminated at a slightly reduced pressure (400 torr). After heating for 2 hours to 115° to 120° C., 2.0 parts of glacial acetic acid and one part of piperidine are added, the temperature is increased to 135° C. and the mixture is kept for 2 hours at this temperature. Then the reaction product is completely dissolved. The solution is added to 105 parts of 20% sodium hydroxide solution, whereby the ester is saponified as described in Example 1 and the acid is precipitated and isolated.

If the reaction is carried out in nitrobenzene instead of nitronaphthalene, 2-anilino-5-(1-naphthylamino)-terephthalic acid can be detected in the thin-layer chromatogram of the acid.

EXAMPLE 10

A mixture consisting of 50.0 parts of succinylo-succinic acid dimethyl ester, 75.0 parts of 4-fluoroaniline and 150.0 parts of 4-fluoronitrobenzene is heated under nitrogen to 70° C. and mixed while stirring with 4 parts of 33% hydrochloric acid. Stirring is continued for 15 minutes. The mixture is heated to 110° C. at a pressure of 400 torr within one hour and stirred for another 2 hours at 110° to 115° C. After adding 2 parts of glacial acetic acid and 1 part of piperidine the temperature is increased to 135° to 140° C. and the reaction mixture is stirred for 4 hours at this temperature. The resulting solution is added to 135 parts of 33% sodium hydroxide solution and further processed as described in Example 3. From the alkaline solution the 2,5-bis-(p-fluoroanilino)-terephthalic acid is precipitated with phosphoric acid at a pH value of 4.5. After suction-filtering, washing and drying the acid is obtained with a content of fluorine of 9.8% (calculated: 9.9%).

When using nitrobenzene as oxidizing agent an acid having a content of fluorine of 9.0% is obtained. In the thin-layer chromatogram of this acid 2-anilino-5-(p-fluoroanilino)-terephthalic acid can be detected.

We claim:

1. In a process for the preparation of 2,5-diarylamino-lower alkyl-terephthalates of the formula

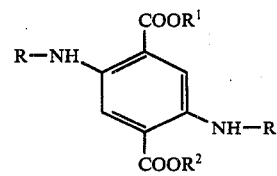

in which $R^1$ and $R^2$, which are the same or different, are alkyl of one to 4 carbon atoms and R has the formula

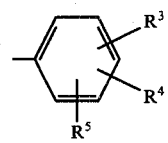

in which $R^3$, $R^4$ and $R^5$ are hydrogen, chlorine, bromine, fluorine, alkyl of one to four carbon atoms, alkoxy of one to four carbon atoms, phenyl or phenoxy or two of the substituents $R^3$, $R^4$ and $R^5$ together stand for a fused benzene nucleus, with the proviso that at least one of the substituents $R^3$, $R^4$ and $R^5$ is not hydrogen, each R having one free ortho-position with respect to the nitrogen atom, by oxidizing a dihydro-2,5-diaryl amino terephthalate of the formula

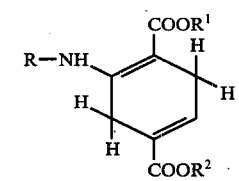

in which R, $R^1$ and $R^2$ are as defined above, with a nitro-aromate in the presence of catalytic amounts of a strong mineral acid or a strong organic acid, the improvement comprising oxidizing said dihydro-2,5-diarylamino terephthalate with a nitro-aromate having the formula

in which R is the same as in said dihydro-2,5-diarylamino terephthalate.

2. A process as claimed in claim 1, wherein the nitro-aromate is selected from the group consisting of o-, m- and p-chloro-, -bromo-, -fluoro-, -methyl- and -methoxy-nitrobenzene, 2-chloro-4-methyl-nitrobenzene, 3-chloro-4-methyl-nitrobenzene, 2,4-dichloro-nitrobenzene, 2,3-dichloro-nitrobenzene or 2,3,4-trichloro-nitrobenzene, 1-nitronaphthalene and 2-nitronaphthalene.

3. A process as claimed in claim 1, wherein the substituent different from hydrogen is in ortho-position.

4. A process as claimed in claim 1, wherein only one of the substituents $R^3$, $R^4$ and $R^5$ is different from hydrogen and linked to the paraposition.

5. A process as claimed in claim 1, wherein two of the substituents $R^3$, $R^4$ and $R^5$ are different from hydrogen, are identical and linked to the 3- and 5-positions.

6. A process as claimed in claim 5, wherein all of the substituents $R^3$, $R^4$ and $R^5$ are different from hydrogen, two identical substituents are in the 3- and 5-positions and the third in 4-position.

7. A process as claimed in claim 1, wherein the oxidation is performed at a temperature of about 110° to 150° C.

8. A process as claimed in claim 1, wherein the nitroaromate is added in an excess.

9. A process as claimed in claim 1, wherein catalytic amounts of said acid are present.

10. A process as claimed in claim 1, wherein said acid is acetic or trifluoroacetic acid.

11. A process as claimed in claim 1, wherein as a co-catalyst a secondary or tertiary amine is added.

12. A process as claimed in claim 11, wherein said co-catalyst is piperidine.

13. A process as claimed in claim 1, wherein the dihydro-2,5-diarylamino terephthalate is formed in situ by reacting a succinylo-succinic acid ester of the formula

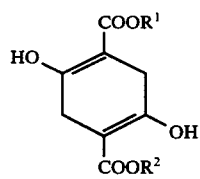

with at least 2 mols of an amine of the formula $R - NH_2$ at a temperature of about 75° to 120° C. in a reaction medium of the formula $R - NO_2$ in which R is the same as in said amine, in the presence of catalytic amounts of an acid.

14. A process as claimed in claim 13, wherein said dihydro-2,5-diarylamino terephthalate is formed in the presence of catalytic amounts of a secondary or tertiary amine.

15. A process as claimed in claim 1, wherein the reaction product is isolated by precipitating it with a low-molecular completely water-soluble alkanol.

16. A process as claimed in claim 1, wherein the reaction product is isolated as the alkalimetal salt of the free acid by adding the reaction mixture to an aqueous alkali metal hydroxide solution and maintaining a temperature of about 90° to 110° C.

17. A process as claimed in claim 16, which is performed in a closed vessel.

* * * * *